(12) United States Patent
Bandyopadhyay et al.

(10) Patent No.: US 8,029,833 B2
(45) Date of Patent: *Oct. 4, 2011

(54) HERBAL COMPOSITION FOR TREATING CD33+ ACUTE AND CHRONIC MYELOID LEUKEMIA AND A METHOD THEREOF

(75) Inventors: Santu Bandyopadhyay, Calcutta (IN); Keshab Chandra Roy, Calcutta (IN); Mitali Ray, Calcutta (IN); Goutam Banerjee, Calcutta (IN); Bikash Chandra Pal, Calcutta (IN); Tanusree Biswas, Calcutta (IN); Samir Bhattacharya, Calcutta (IN)

(73) Assignee: Council of Scientific and Industrial Research, New Delhi (IN)

( * ) Notice: Subject to any disclaimer, the term of this patent is extended or adjusted under 35 U.S.C. 154(b) by 68 days.

This patent is subject to a terminal disclaimer.

(21) Appl. No.: 12/623,476

(22) Filed: Nov. 23, 2009

(65) Prior Publication Data

US 2010/0068314 A1    Mar. 18, 2010

Related U.S. Application Data

(60) Division of application No. 11/730,433, filed on Apr. 2, 2007, now Pat. No. 7,674,487, which is a division of application No. 10/960,064, filed on Oct. 8, 2004, now Pat. No. 7,306,817, which is a division of application No. 10/207,039, filed on Jul. 30, 2002, now Pat. No. 6,852,344, which is a continuation-in-part of application No. 09/772,003, filed on Jan. 30, 2001, now abandoned.

(60) Provisional application No. 60/384,163, filed on May 31, 2002.

(30) Foreign Application Priority Data

Dec. 4, 2000    (WO) ............... PCT/IN00/00118

(51) Int. Cl.
*A61K 36/67*    (2006.01)
*A61P 35/02*    (2006.01)

(52) U.S. Cl. ......... 424/769; 424/774; 424/725; 514/908
(58) Field of Classification Search .................. None
See application file for complete search history.

(56) References Cited

U.S. PATENT DOCUMENTS

| 5,389,371 | A | 2/1995 | Shiao ..................... 424/195.1 |
| 5,582,822 | A | 12/1996 | Brandely et al. .......... 424/85.2 |
| 6,610,332 | B2 | 8/2003 | Bandyopadhyay et al. .. 424/769 |
| 6,852,344 | B2 | 2/2005 | Bandyopadhyay et al. .. 424/769 |
| 7,306,817 | B2 | 12/2007 | Bandyopadhyay et al. .. 424/734 |

FOREIGN PATENT DOCUMENTS

| JP | 401261403 A | 10/1989 |
| JP | 09278666 A | 10/1997 |
| JP | 10077495 A | 3/1998 |
| JP | 11130685 A | 5/1999 |

OTHER PUBLICATIONS

Wealth of India, vol. 8, pp. 84-95, (1969): New Delhi, India.
Sengupta et al., Indian Journal of Experimental Biology (Apr. 2000), vol. 38, 338-342.
Sadasivan et al., Mutation Research, Chromosome-Damaging Effect of Betel Leaf, (1978), vol. 57, pp. 183-185.
Van De Graaff et al., Concepts of Human Anatomy and Physiology, WCB Publishers, (1986) pp. 159, 618, 706-709.
Database WPI, Section CH, Week 199930, Derwent Publications Ltd., London, BG; AN 1999-352797, XP002174279 (JP 11 130685 A).
Database WPI, Section CH, Week 199702, Derwent Publications Ltd., London, BG; AN 1997-017312, XP002174280 (JP 08 283171 A).
Mori H et al., "Carcinogenicity Examination of Betel Nuts and Piper Betel Leaves", Experientia (1979), vol. 35, No. 3, pp. 384-385. ISSN: 0014-4754, XP001008625.

*Primary Examiner* — Michele Flood
(74) *Attorney, Agent, or Firm* — Fitzpatrick, Cella, Harper & Scinto (57) ABSTRACT

A method of treating CD33+ acute and chronic myeloid leukemia in animals including humans, using fraction nos. 1 and 9 obtained from water:methanol fraction by column chromatography, with ratio of water and methanol ranging between 1:5 to 5:1, wherein said water:methanol fraction is obtained from the polar extract of *Piper betel* by HPLC, with retention time of 3.6 and 24.0 minutes respectively, with said fractions used both individually, and in combination.

20 Claims, 8 Drawing Sheets

FIG. 1a — PBMC + MEDIA

FIG. 1b — PBMC + BETEL LEAF EXTRACT

HERBAL COMPOSITION FOR TREATING CD33+ ACUTE AND CHRONIC MYELOID LEUKEMIA AND A METHOD THEREOF

CROSS-REFERENCE TO RELATED APPLICATIONS

This is a Divisional of U.S. application Ser. No. 11/730,433, filed on Apr. 2, 2007, which is a Divisional of U.S. application Ser. No. 10/960,064, now U.S. Pat. No. 7,306,817, filed on Oct. 8, 2004, which is a Divisional of U.S. application Ser. No. 10/207,039, filed Jul. 30, 2002, now U.S. Pat. No. 6,852,344, which is a Continuation-in-Part of U.S. application Ser. No. 09/772,003, filed Jan. 30, 2001, now abandoned, and Provisional Application No. 60/384,163, filed May 31, 2002.).

Applicants submit a copy of the Substitute Specification as previously submitted in the parent application to incorporate the amendments made to FIGS. 2, 4, 5, and 6. No new matter has been added.

FIELD OF INVENTION

This invention also relates to a method of treating Myeloid leukemia using the *betel* leaf extract to an animal including human beings suffering from Myeloid leukemia. Further, this invention also relates to a herbal based composition for treatment of CD33+ acute and chronic myeloid leukemia by *Piper betel* leaf extracts, fractions of *Piper betel* leaf extracts and 3-O-p-coumaryl quinic acid purified from *Piper betel* leaves extract.

BACKGROUND AND PRIOR ART REFERENCES

*Betel* leaves have a strong pungent aromatic flavor and are widely used as a masticatory. Generally, mature or over mature leaves, which have ceased growing but not yet become brittle are used for chewing. The basic preparation for chewing purposes consists of *betel* leaf smeared with hydrated lime and *catechu* to which scrapings of *arecanut* are added; flavorings such as coconut shavings, clove, cardamom, fennel, powdered liquorice, nutmeg and also tobacco are used according to one's taste. In some places prepared pan is covered with silver or gold leaf. As a masticatory, it is credited with many properties: it is aromatic, digestive, stimulant and carminative.

Medicinally it is useful in catarrhal and pulmonary infections; it is also used for poultices. The effects of chewing of *betel* with *arecanut* and other adjuncts are the excitation of the salivary glands and the irritation of the mucous membrane of the mouth. The red coloration produced is due to a pigment in the *arecanut*, which manifests itself under the action of alkali in time and *catechu*. A mild degree of stimulation is produced, resulting in a sensation of warmth and well being, besides imparting a pleasant odor. The most important factor determining the aromatic value of the leaf is the amount and particularly the nature of the essential oil present. *Betel* leaves from different regions vary in smell and taste. The most pungent is the Sanchi type, while the most mild and sweet ones are from Madras.

The *betel* leaves contain essential oils, the content of oil varies from 0.7 to 2.6 percent depending upon the varieties of leaves. The oil consists of phenols and terpens. The higher the proportion of phenol oil, the better the quality. An isomer of eugenol named chavibetol (*betel* phenol; 4-allyl-2-hydroxy-1-methoxy benzene) is considered to be the characteristic constituent of *betel* oil. It is however, absent in Indian samples. *Betel* oil of Indian types contain as a predominant phenolic constituent. Oil of *betel* has been used in the treatment of various respiratory catarrhs, under as a local application either by gargle or by inhalation in diphtheria. It has carminative properties. It exhibits in different action on the central nervous system of mammals; lethal doses produce deep narcosis leading to death with a few hours.

The essential oil and extracts of the leaves possess activity against several Gram-positive and Gram-negative bacteria such as *Micrococcus pyogenes* var. *albus, Bacillus subtilis* and *B. megaterium, Diplococcus pneumoniae, Streptococcus pyogenes, Escherichia coli, Salmonella typhosa, Vibrio comma, Shigella dysenteriae, Proteus vulgaris, Pseudomonas solanacaerum, Sarcina lutea* and *Erwinia carotorora*. The essential oil and leaf extracts also showed antifungal activity against *Asperigillus niger* and *A. oryzae, Curvularia lunata* and *Fusarium oxysporum*. The oil is found to be lethal in about 5 minutes to the protozoa *Paramaeceum caudatum* (Wealth of India, Vol. 8, pg. 84-94). It inhibits the growth of *Vibrio cholerae, Salmonella typhosum* and *Shigella flexneri* and *Escherichia coli*. Steam—distillate of the leaves showed activity against *Mycobacterium tuberculosis*.

Myeloid leukemia is usually subdivided into two groups: Acute Myeloid Leukemia (AML) and Chronic Myeloid Leukemia (CML). AML is characterized by an increase in the number of myeloid cells in the marrow and an arrest in their maturation, frequently resulting in hematopoietic insufficiency. In the United States, the annual incidence of AML is approximately 2.4 per 100,000 and it increases progressively with age to a peak of 12.6 per 100,000 adults 65 years of age or older. Despite improved therapeutic approaches, prognosis of AML is very poor around the globe. Even in the United States, five-year survival rate among patients who are less than 65 years of age is less than 40%. During the last decade this value was 15. Similarly, the prognosis of CML is also very poor in spite of advancement of clinical medicine.

Myeloid leukemia, both acute (AML) and chronic (CML) are lethal, there is no drug directing towards the destruction of the myeloid cells and these cells poorly respond to chemotherapy, which is always non-specific, thus adversely affecting normal cells. Unique property of the therapy with *Piper betel* components is the killing of myeloid cancer cells by recognizing CD33+ marker on the cell membrane, leaving normal cells without getting affected.

Japanese Patent No. JP 63089744 titled new substance and anticancer drug refers to using *betel* palm extracts as anticancer drug. Here, Applicant would like to clarify that *betel* palm and *piper betel* are two different things. *Piper betel* belongs to pepper family called Piperaceae, whereas *betel* Palm belongs to Palm family Arecaceae. The list of websites that establish the statement made by the Applicant is as shown below.

www.school.discovery.com
www.undcp.com
www.channels.apollolife.com
www.newscrops.uq.edu.au Further, its is a known fact that there are hundreds of type of cancers and each cancer condition is a reflection of different causative factors and different cellular behaviors.

Applicants work is extremely specific and there is no reference in this cited art to provide any idea regarding potential of said extract from *piper betel* in the treatment of myeloid leukemia. As mentioned earlier, each type of cancer leads to its own peculiar health condition and one compound capable of treating one type of cancer may not be considered to be useful in treating other types of cancer also. All this requires considerable amount of scientific understanding and years of experimentation."

Further, the Applicant of the instant Application has worked on specificity and is been able to establish that *piper betel* extract has anti-monocytic activity and said activity can be use in the treatment of myeloid leukemia. Therefore, *Betel* palm can not be considered to cure any type of cancer.

Sengupta et al in Indian Journal of Experimental Biology Vol. 38, April 2000, pp. 338-342 year 2002 refers to toxicity evaluation of extract from *piper betel* Linn. and make an observation that the said extract cause reduction of total white blood cell (W.B.C.) count. Here, Applicants would like to clarify that White blood cells are consisting of basophils, eosinophils, neutrophils, lymphocytes, and monocytes. The cited art refers to mere decrease in the total W.B.C counts. The decrease in W.B.C count could be decrease in any of the five constituents of W.B.C.

In addition, it is seen that activation or suppression of one type of W.B.C. will not automatically lead to similar behavior by other type. There are instances where activation to a particular stimuli will be restricted to only one type of W.B.C. for example allergy leads to increase in the number of basophils but levels of other type of W.B.C.s remains more or less constant.

Further it is also seen that activation of T-lymphocytes will not always lead to corresponding activation of B-lymphocytes. So basically, the behavior of each of this type of W.B.C. is not identical and thus reduction in levels of one type of W.B.C. will not always pull the levels of other type of W.B.C. also. Though the total W.B.C. will definitely come down.

Since the cited art merely refers to decrease in the levels of W.B.C. with *piper betel* Linn. and make no reference to the decrease in the level of monocytes, it is considered not at all enabling as to the invention of Applicant.

Further, the cited art involves in vivo studies on rat, wherein the rats have been exposed to high dose of *piper betel* leaf stalk. Also, the exposure is for as long as 60 days. Now, under conditions like high dose and that too for such a long duration, the change in the levels of W.B.C. and R.B.C. can not be interpreted in terms of medicinal aspects. The whole purpose of conducting the experiment in the cited art was to understand the toxicology of the *piper betel*. The decrease in the levels of W.B.C. count refers to change in the levels of W.B.C. under extreme conditions.

In addition, the percentage content of the monocytes in the total W.B.C. is not more than 3-7 percent. Therefore, the decrease in the levels of W.B.C. in the cited art cannot help one conclude that the total decrease is due to decrease in the levels of monocyte and only monocytes and not any other kinds of W.B.C.

Myeloid leukemia is usually subdivided into two groups: Acute Myeloid Leukemia (AML) and Chronic Myeloid Leukemia (CML). AML is characterized by an increase in the number of myeloid cells in the bone marrow and an arrest in their maturation. In the United States, the annual incidence of AML is approximately 2.4 per 100,000 and it increases progressively with age, to a peak of 12.6 per 100,000 in adults of 65 years age or older. The CML is a malignant clonal disorder of hematopoietic stem cells. The median age at presentation is 53 years, but it occurs at all age groups, including children.

The natural history of CML is progression from a benign chronic phase to a rapidly fatal blast crisis within three to five years or even earlier. The prognosis of CML is also poor inspite of vast advancement of clinical medicine (1). CD33 represents a specific and useful marker in the process of myeloid cell differentiation (2). Recent reports suggest that engagement of CD33 by monoclonal antibody induced apoptosis leading to growth inhibition of proliferation of AML and CML cells in vitro (2,3). Exploiting the myeloid specific expression of CD33, humanized anti-CD33 monoclonal antibody conjugated with anti-cancer drug has been tried in AML patients with significant success (4). With the extract from *Piper betel* leaves anti-myeloid activity was claimed earlier (Patent filed no. PCT/INOO/00118 dated Dec. 12, 2000).

Hence, Applicant's earlier finding is in directed consonance with the present patent filing on *Piper betel* leaf extract, fractionated leaf extracts and purified compound 3-O-p-coumaryl quinic acid (FIG. 3) obtained from leaf extract for treating CD33+ acute and chronic myeloid leukemia.

*Piper betel* leaves have a strong pungent aromatic flavour and are widely used in India as a masticatory. Generally, mature or overmature leaves, which have ceased growing but not yet become brittle are used for chewing. The basic preparation for chewing purposes consists of *betel* leaf smeared with hydrated lime and *catechu* to which scrapings of *arecanut* are added; flavourings such as coconut shavings, clove, cardamom, fennel, powdered liquorice, nutmeg and also tobacco are used according to one's taste. In some places prepared *Piper betel* leaf preparation is covered with silver or gold film. As a masticatory, it is credited with many properties: it is aromatic, digestive, stimulant and carminative.

Medicinally it is useful in catarrhal and pulmonary infections; it is also used for poultices. The effects of chewing of *betel* leaves with *arecanut* and other adjuncts are the excitation of the salivary glands and the irritation of the mucous membrane of the mouth. The red coloration produced is due to a pigment in the *arecanut*, which manifests itself under the action of alkali in lime and *catechu*. A mild degree of stimulation is produced, resulting in a sensation of warmth and well-being, besides imparting a pleasant odour. The most important factor determining the aromatic value of the leaf is the amount and particularly the nature of the essential oil present.

*Betel* leaves from different regions vary in smell and taste. The most pungent is the Sanchi type, while the most mild and sweet ones are from Varanasi. The *betel* leaves contain essential oils, the content of oil varies from 0.7 to 2.6 percent depending upon the varieties of leaves. The oil consists of phenols and terpens. The higher the proportion of phenol the better the quality. An isomer of eugenol named chavibetol (*betel* phenol; 4-alkyl-2-hydroxy-1methoxy benzene) is considered to be characteristic constituent of *betel* oil. *Betel* oil of Indian types contains a predominant phenolic constituent and used in the treatment of various respiratory problems, either as a local application or by gargle. It has carminative properties. It exhibits in different actions on the central nervous system of mammals.

The essential oil and extracts of the leaves possess activity against several Gram-positive and Gram-negative bacteria such as *Micrococcus pyogenes* var. *Albus, Bacillus subtilis* and *B. Megaterium, Diplococcus pneumoniae, Streptococcus pyogenes, Escherichia coli, Salmonella typhosa, Vibrio comma, Shigella dysenteriae, Proteus vulgaris, Pseudomonas solanacaerum, Sarcina lutea* and *Erwinia carotorora*.

The essential oil and leaf extracts also showed anti-fungal activity against *Asperigillus niger* and *A. Oryzae, Curvularia lunata* and *Fusarium oxysporum*. The oil is found to be lethal in about 5 minutes to the protozoa, *Paramaeceum caudatum* (5). Steam-distillate of the leaves showed activity against *Mycobacterium tuberculosis*. Some of the references are as follows: 1. Sawyers C L, The New England Journal of Medicine, 340 (17), 1330-1340, 1999; 2. Vitale, C; Romagnani, C, et al., Proc. Natl. Acd. Sci. USA, 96 (26), 15091-15096, 1999; 3. Vitale, C et al., Proc. Natl. Acd. Sci, USA., 98 (10), 5764-5769, 2001; 4. Sievers E L, Appelbaum, F R et al., Blood, 93, 3678-3684, 1999.

OBJECTS OF THE PRESENT INVENTION

The main object of the invention is for treating myeloid leukemia in animals including human beings using *betel* leaf extract.

Another object is to provide a composition comprising *betel* leaf extract useful for the treatment of myeloid leukemia.

Yet another object of the invention is to provide a new herbal-based composition for the treatment of CD33+ acute and chronic myeloid leukemia by *Piper betel* leaf extracts.

Still another object of the invention is to provide a process for the isolation of active fractions from leaves or any other plant parts of *Piper betel* to treat CD33+ AML and CML.

Still another object of the invention is to provide a simplified method of isolation of active components from all plant parts of *Piper betel* possessing biological activities relevant to the treatment of CD33+ AML and CML.

Still another object of the invention is to provide a new herbal product from active fraction from leaves or any other plant parts of *Piper betel* for the treatment of CD33+ AML and CML.

Still another object of the invention is to provide a herbal compound 3-O-p-coumaryl quinic acid purified from leaves of *Piper betel* for the treatment of CD33+ AML and CML.

Still another object of the invention is to provide a process for the preparation of extract from leaves or any other plant parts of *Piper betel* for the treatment of CD33+ AML and CML.

Still another object of the invention is to provide a simplified method of extract preparation from leaves or any other plant parts of *Piper betel* for the treatment of CD33+ AML and CML.

Still another object of the invention is to provide a process for the preparation of 3-O-p-coumaryl quinic acid from leaves of *Piper betel* for the treatment of CD33+ AML and CML.

Still another object of the invention is to provide a simplified method of preparation of 3-O-p-coumaryl quinic acid from all plant parts of *Piper betel* for the treatment of CD33+ AML and CML.

SUMMARY OF THE INVENTION

To meet the above objects, the invention provides anti monocytic activity of *betel* leaf extract and this activity is employed for treating myeloid leukemia in animals including human beings.

DETAILED DESCRIPTION OF THE INVENTION

Accordingly, the present invention relates to a method of treating CD33+ acute and chronic myeloid leukemia in animals including humans, using fraction nos. 1 and 9 obtained from water:methanol fraction by column chromatography, with ratio of water and methanol ranging between 1:5 to 5:1, wherein said water:methanol fraction is obtained from the polar extract of *piper betel* by HPLC, with retention time of 3.6 and 24.0 minutes respectively, with said fractions used both individually, and in combination, and a composition comprising the said fraction nos. 1 and 9.

In an embodiment of the present invention, wherein a method of treating Myeloid leukemia in animals including human beings using the *betel* leaf extract, lyophilized extract or a composition comprising *betel* leaf extract, said method comprising administering a pharmaceutically effective amount of *betel* leaf extract, lyophilized extract or a composition comprising *betel* leaf extract to an animal including human beings suffering from Myeloid leukemia.

In another embodiment of the present invention, wherein the composition comprising *betel* leaf extract associated with or in combination with a pharmaceutically acceptable additive.

In yet another embodiment of the present invention, wherein the additive is selected in such a manner that does not interfere with the activity of *betel* leaf extract.

In still another embodiment of the present invention, wherein the additive is selected from nutrients such as proteins, carbohydrates, sugar, talc, magnesium stearate, cellulose, calcium carbonate, starch-gelatin paste and/or pharmaceutically acceptable carriers, excipient, diluent or solvent.

In still another embodiment of the present invention, wherein the *betel* leaf extract or the composition is administered orally or intramuscularly.

In still another embodiment of the present invention, wherein the oral route is in the form of capsule, syrup, concentrate, powder or granules.

In still another embodiment of the present invention, wherein the ratio of *betel* leaf extract to the additive is in the range between 1-10: 10-1.

In still another embodiment of the present invention, wherein the *betel* leaf extract is obtained by crushing the *betel* leaf or extracting the crushed leafs with water or organic solvents such as alcohol, carbontetrachloride, chloroform and acetone.

In still another embodiment of the present invention, wherein the *betel* leaf extract or the composition administered at a dosage level between 5 to 20 mg/kg of body weight for alternate days for one month.

In still another embodiment of the present invention, wherein the composition reduces the viability of monocytes by 80%.

In an embodiment of the present invention, wherein a method of destroying monocytes present in human peripheral mononuclear cells (PBMCs) for treating myeloid leukemia, using *betel* leaf extract, lyophilized extract or a composition comprising *betel* leaf extract and a pharmaceutically acceptable additive, said method comprising treating PBMCs with a pharmaceutically effective amount of *betel* leaf extract, lyophilized extract or a composition comprising *betel* leaf extract and a pharmaceutically acceptable additive.

In another embodiment of the present invention, wherein the human PBMCs are treated with the said extract or composition for overnight.

In still another embodiment of the present invention, wherein the destruction of monocytes is detected by using flow cytometry.

In still another embodiment of the present invention, wherein said method reduces the viability of monocytes at least by 80%.

In still another embodiment of the present invention, wherein said extract or composition shows no adverse effect on lymphocytes.

In still another embodiment of the present invention, wherein the myeloid leukemia is treated by using the said extract or the composition at a dosage level between 5 to 20 mg/kg body weight for alternate days for one month.

In still another embodiment of the present invention, wherein the *betel* leaf extract or the composition is administered orally or intramuscularly.

In still another embodiment of the present invention, wherein the said extract and the composition for the oral route is in the form of capsule, syrup, concentrate, powder, or granules.

In still another embodiment of the present invention, wherein the *betel* leaf extract is obtained by crushing the *betel* leaf or extracting the crushed leafs with water or organic solvents such as alcohol, carbon tetrachloride, chloroform, and acetone.

In still another embodiment of the present invention, wherein the additive is selected in such a manner that it does not interfere with the activity of *betel* leaf extract.

In still another embodiment of the present invention, wherein additive is selected from nutrients such as proteins, carbohydrates, sugar, talc, magnesium stearate, cellulose, calcium carbonate, starch-gelatin paste and/or pharmaceutically acceptable carriers, excipient, diluent or solvent.

In still another embodiment of the present invention, wherein ratios of *betel* leaf extract to the additive is in the range between 1-10:1-10.

In still another embodiment of the present invention, wherein a method of treating CD33+ both acute and chronic myeloid leukemia in mammals including humans, using water:methanol fraction nos. 1 and 9 obtained from polar extract of *piper betel* by HPLC, with retention time of 3.6 and 24.0 minutes respectively, with said fractions used both individually, and in combination, said method comprising steps of:

exposing a patient of myeloid leukemia with the said fraction(s) intravenously, and observing reduction in the levels of myeloid leukemia cells in the patient.

In still another embodiment of the present invention, wherein ratio of water and methanol is ranging between 1:5 to 5:1.

In still another embodiment of the present invention, wherein fraction no. 9 is compound 3-O-p-coumaryl quinic acid.

In still another embodiment of the present invention, wherein the compound 3-O-p-coumaryl quinic acid of fraction no. 9 is more effective in acute myeloid leukemia as compared to chronic myeloid leukemia.

In still another embodiment of the present invention, wherein purified compound 3-O-p-coumaryl quinic acid of fraction 9 shows 100% efficacy against acute myeloid leukemia at concentration about 600 µg/ml.

In still another embodiment of the present invention, wherein dosage of each fraction individually ranging between 200-500 mg/day.

In still another embodiment of the present invention, wherein dosage of fraction nos. 1, and 9 in combination is ranging between 125 to 370 mg/day.

In still another embodiment of the present invention, wherein ratio of dosage of fraction nos. 1 and 9 is ranging between 0.1:5 to 5:0.1, preferably, 1:1.

In still another embodiment of the present invention, wherein fraction 1 is more efficient as compared to fraction 9.

In still another embodiment of the present invention, wherein combination of fractions 1 and 9 is more effective in the management of myeloid leukemia as compared to the said fractions alone.

In another embodiment of the present invention, wherein a composition useful for treating CD33+ acute and chronic myeloid leukemia in animals including humans, said composition comprising water:methanol fraction nos. 1 and 9 obtained from polar extract of plant *piper betel* by HPLC, with retention time of 3.6 and 24.0 minutes respectively, with said fractions used both individually and in combination.

In another embodiment of the present invention, wherein the fraction 9 contains compound 3-O-p-coumaryl quinic acid.

In yet another embodiment of the present invention, wherein A method of isolating biologically active fraction nos. 1 and 9 from the water:methanol fraction, obtained from polar extract of plant *piper betel*, said method comprising steps of:

a. cutting the plant parts into small pieces, b. homogenizing the said pieces with polar solvent to obtain an extract, c. filtering the extract to collect filterate, d. lyophilizing the clear extract solution to obtain a semi-solid mass, e. fractionating the said semi-solid mass using column chromatography with only water, water-methanol with ratio ranging between 1:5 to 5:1, and only methanol, as eluents, f. selecting water:methanol fraction from the column chromatography, g. running HPLC with flow rate of 1.0 ml/min, using solvent system of methanol:water:acetic acid of ratio about 23:76:1, h. detecting about 12 peaks at about 280 nm, with varied retention time ranging between 3.6 to 36 minutes, i. separating the said peaks in a preparative HPLC with flow rate of 12 ml/min, and j. obtaining fraction nos. 1 and 9 having desired biological activity.

In still another embodiment of the present invention, wherein the fraction 9 contains compound 3-O-p-coumaryl quinic acid.

In still another embodiment of the present invention, wherein optionally, centrifuging the filterate to obtain a clear solution before fractionating.

In still another embodiment of the present invention, wherein ratio of dosage of fraction nos. 1 and 9 is ranging between 0.1:5 to 5:0.1, preferably 1:1.

In an embodiment of the present invention, wherein accordingly, the present invention provides a new use of *betel* leaf extract namely anti monocytic activity. This anti Monocytic activity of *betel* leaf extracts is used for treating myeloid leukemia in animals including human beings.

In another embodiment, a pharmaceutical composition useful for the treatment of myeloid leukemia, said composition comprising effective amount of *betel* leaf extract together with or associated with a pharmaceutically acceptable additive.

In yet another embodiment of the invention, the additive is selected in such a manner it does not interfere with the activity of *betel* leaf extract.

In still another embodiment of the invention, the additive is selected from nutrients such as proteins, carbohydrates and sugar, talc, magnesium sterate, cellulose, calcium carbonate, starch-gelatin paste and/or pharmaceutically acceptable carriers, excipient, diluent or solvent.

In still another embodiment of the invention, the *betel* leaf extract or the composition is administered orally or intramuscularly.

In still another embodiment of the invention, the oral route is in the form of capsule, syrup, concentrate, powder or granules.

In still another embodiment of the invention, the ratio of *betel* leaf extract to the additive is in the range between 10 to 1.

In still another embodiment of the invention, the *betel* leaf extract or the composition is administered at a dosage level between 5 to 20 mg/kg of body weight for alternate days for one month.

In still another embodiment of the invention, the *betel* leaf extract or the composition reduces the monocytes content by 80%.

In still another embodiment of the invention, the *betel* leaf extract or the composition is used for the treatment of myeloid leukemia.

In still another embodiments of the invention, the *betel* leaf extract is administered together with or associated with a pharmaceutically acceptable additive.

In still another embodiment of the invention, the additive is selected in such a manner it does not interfere with the activity of *betel* leaf extract.

In still another embodiment of the invention, the additive is selected from nutrients such as proteins, carbohydrates and sugar, talc, magnesium stearate, cellulose, calcium carbonate, starch-gelatin paste and/or pharmaceutically acceptable carriers.

In still another embodiment of the invention, the *betel* leaf extract or the composition is administered orally or intramuscularly.

In still another embodiment of the invention, the oral route is in the form of capsule, syrup, concentrate, powder or granules.

In still another embodiment of the invention, the ratio of *betel* leaf extract to the additive is in the range between 10 to 1.

In still another embodiment of the invention, the *betel* leaf extract or the composition is administered at a dosage level between 5 to 20 mg/kg of body weight for alternate days for one month.

In still another embodiment of the invention, the *betel* leaf extract or the composition reduces the viability of monocytes by 80%.

In still another embodiment of the invention, the *betel* leaf extract is obtained by crushing the *betel* leaf or extracting the crushed leafs with water or organic solvents such as alcohol, carbontetrachloride, chloroform and acetone.

Another embodiment of the present invention provides the preparation of *betel* leaf extracts comprising the following steps:
1) washing of the fresh leaves of *Piper betel* and homogenizing in a mixture blender;
2) sonicating in an ultrasonic bath with 2 to 3 bursts each for 15 minutes and filtering the extract, if desired repeating the extraction at least once and drying; and
3) lyophilizing the extract to get a semi-solid mass Yet another embodiment of the invention, the *betel* leaf (*Piper betel*) is selected from the following types namely Wild type, Climber type, Bangla type and Sweet type.

Accordingly, the present invention provides an herbal-based composition from *piper betel* leaves for the treatment of CD33+ acute and chronic myeloid leukemia.

Doses for myeloid leukemia patient depends on the in-vitro efficiency of the drug from *piper betel* either individually or in combination, the doses of in-vitro application for human myeloid cancer patients may range from 200 mg to 500 mg per day per patient if given as individual fraction (fraction 1 or fraction 9) or as a combination of fraction 1 and fraction 9 in the ratio between 0.1:5 to 5.0.1 preferably in the ratio 1:1 totaling 125 mg to 370 mg per day per patient through intravenous route.

In an embodiment of the invention relates to evaluation of bioactivity of fractions 1 to 9 isolated from *piper betel* leaf against cancer cells.

In an embodiment of the invention relates to evaluation of bioactivity of fractions 1 to 9 isolated from *piper betel* leaf for the treatment of CD33+ acute and chronic myeloid leukemia.

In still embodiment of the invention, wherein invention also provides a process for isolation of 3-O-p-coumaryl quinic acid from *piper betel*, which is reported for the first time.

In still another embodiment of the invention, wherein said invention relates to a process for the isolation of active fractions from leaves or any other plant parts of *Piper betel* to treat CD33+ AML and CML.

In still another embodiment of the invention, wherein said invention relates to a simplified method of isolation of active components from all plant parts of *Piper betel* possessing biological activities relevant to the treatment of CD33+ AML and CML.

In still another embodiment of the invention, wherein said invention relates to a new herbal composition/fraction from leaves or any other plant parts of *Piper betel* for the treatment of CD33+ AML and CML.

In still another embodiment of the invention, wherein said invention relates to new activity of compound 3-O-p-coumaryl quinic acid purified from leaves of *Piper betel* for the treatment of CD33+ AML and CML.

In still another embodiment of the invention, wherein said invention relates to a process for the preparation of extract from leaves or any other plant parts of *Piper betel* for the treatment of CD33+ AML and CML.

In still another embodiment of the invention, wherein said invention relates to simplified method of extract preparation from leaves or any other plant parts of *Piper betel* for the treatment of CD33+ AML and CML.

In still another embodiment of the invention, wherein said invention relates to a process for the preparation of 3-O-p-coumaryl quinic acid from leaves of *Piper betel* for the treatment of CD33+ AML and CML.

In still another embodiment of the invention relates to a simplified method of preparation of 3-O-p-coumaryl quinic acid from all plant parts of *Piper betel* for the treatment of CD33+ AML and CML.

BRIEF DESCRIPTION OF THE ACCOMPANYING DRAWINGS

FIGS. 1(*a*) and 1(*b*) represents destruction of monocytes from human PBMC after incubation with *betel* leaf extract.

FIG. 4 represents destruction of CD33+ myeloid leukemia cells in vitro by *P. Betel* leaf extract as demonstrated by flow cytometry. Data is presented as histograms. In upper panels, Forward Scattering of light (X-axis) is plotted against the cell numbers (counts Y-axis). In the lower panels, side scattering of light (X-axis) is plotted against the cell numbers. Solid lines represent data with myeloid leukemia cells before treatment with *P. betel* leaf extract and the dotted lines represent data with myeloid leukemia cells after treatment with *P. betel* leaf extract (10.0 mg/ml) for 48 hours. Specifically, FIG. 4(*a*) represents variation in the number of CD33− myeloid leukemia cells on exposure to forward scattering of light; FIG. 4(*b*) represents variation in the number of CD33− myeloid leukemia cells on exposure to side scattering of light; FIG. 4(*c*) represents variation in the number of CD33+ myeloid leukemia cells on exposure to forward scattering of light; and FIG. 4(*d*) represents variation in the number of CD33+ myeloid leukemia cells on exposure of side scattering of light.

FIG. 5 represents destruction of CD33+ myeloid leukemic cells in vitro by fraction E as demonstrated by flow cytometry. Dot plots of Forward Scatter vs. Side Scatter with CD33+ myeloid leukemic cells before and after treatment with fraction E (100.0 μg/ml) for 48 hours are shown in left panels where gated region (R1) represents myeloid leukemic cells. Two colour dot plots are also shown after staining with fluorescein isothiocyanate (FITC) conjugated anti-CD33 and phycocrytbrin (PE) conjugated anti-CD13 monoclonal antibodies. Isotype matched control antibodies (FITC and PE conjugated) were used as negative controls. Upper left quadrants represented CD13, CD33+ cells and upper right quadrants represented CD13+, CD33+ cells. Specifically.

FIG. 6 represents CD33− myeloid leukemic cells are unaffected by fraction E as demonstrated by flow cytometry. Two colour dot plots after staining CD33− myeloid leukemic cells with anti-CD33-FITC and anti-CD13-PE monoclonal antibodies before and after treatment with fraction E (100.0 μg/ml) for 48 hours are shown. Isotype matched control monoclonal antibodies (FITC and PE labelled) were used as negative controls. Upper left quadrants represented CD13+, CD33 cells and upper right quadrants represented CD13+, CD33+ cells. Specifically.

The following examples are given by way of explanation and for illustration only and these examples should not be construed in any manner to limit the scope of the invention.

EXAMPLE 1

34.14 gm of fresh leaves of *Piper betel* thoroughly washed in sterile water was homogenized with 100 ml of glass distilled water in a mixture-blender. It was then sonicated in an ultrasonic bath with 3 burst each for 15 min. The extract was filtered through Whatman No. 1 filter paper and the filtrate was collected. This process of extraction was repeated three times. The combined extract was lyophilized yielding a semisolid mass weighing 1.17 gm. This was then tested for biological activity.

EXAMPLE 2

The fresh leaves of *Piper betel* weighing 21.68 gm homogenized with distilled water (60 ml) in a mixture-blender and then sonicated in an ultrasonic bath with 2 burst each for 15 min. It was allowed to be extracted overnight or 16 hours. Filtering through Whatman No. 1 filter paper separated the material extracted in water. This type of treatment for extraction was repeated for three times. The combined extract was evaporated to dryness in a flash evaporator under reduced pressure at 45° C. The residual substance was then dried in a desiccator under high vacuum and the semi-solid mass weighing 0.59 gm was tested for biological activity.

Properties of the Extract Material:

The biologically active material obtained by examples 1 and 2 has the following properties:
1) The dried semisolid prepared as stated above was a dark colored material soluble in water and dimethyl sulfoxide.
2) Thin layer chromatography of the active material shows five spots having $R_f$ 0.75, 0.64, 0.50, 0.40 and 0.33 in the solvent system of n-butanol, acetic acid and water in the ratio of 9:5:7 respectively.
3) The HPLC analysis of the active material using Intersil ODS-3 (4.6×250 mm) analytical column, solvent system methanol and water in the ratio of 4:1 and a flow rate of 1.0 ml/min., detection at 217 nm resolved the material into eleven peaks with the retention time of 2.69, 4.27, 5.95, 6.97, 7.49, 9.39, 11.20, 12.40, 15.53, 18.90 and 21.49 mins.

EXAMPLE 3

(a) Preparation of Human Peripheral Blood Mononuclear Cells (PBMC)

Heparinized whole blood (collected from normal individuals) was subjected to Ficoll Hypaque density gradient centrifugation. Cells in the interface were washed twice with phosphate buffered saline (PBS) and then re-suspended in medium RPMI-1640 supplemented with 10%. Fetal Bovine Serum.

(b) Incubation of Hpbmc with *Betel* Leaf Extract

PBMC ($5.0 \times 10^6$ cells) were cultured overnight (18 hours) at 37° C. in 5% $CO_2$ in a total volume of 2.0 ml RPMI+10% FBS in 24 well plates in the presence or absence of *betel* leaf extracts (12.5-mg/ml final concentration). At the end of the incubation period, PBMC were washed twice with PBS and used for flow cytometry for the detection of Monocyte destruction.

(c) Monitoring of Light Scattering Induced by Lymphocytes and Monocytes by Flow Cytometry hPBMC were incubated with *betel* extracts, washed with PBS once and resuspended in PBS containing 1% paraformaldehyde. Cells were analyzed in a flow cytometer (FACS Calibur, Becton Dickinson)

(d) Results

Figure 1A:
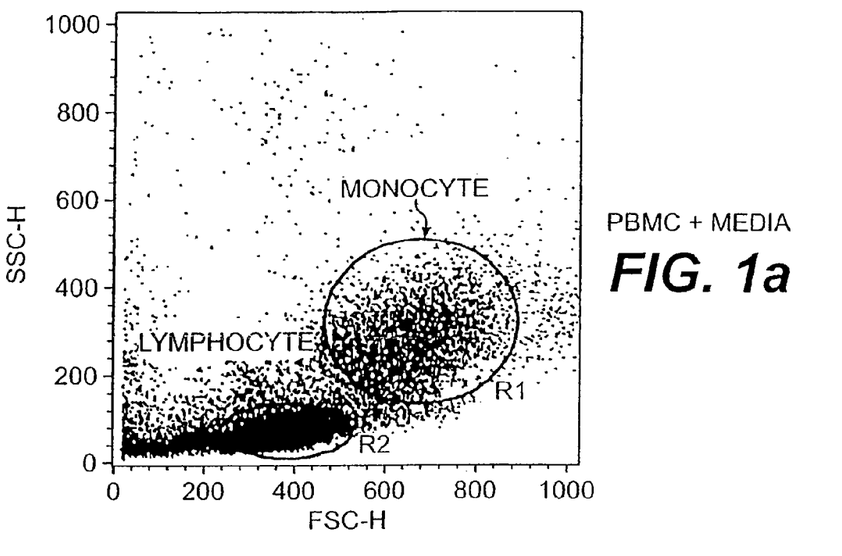
Figure 1B:
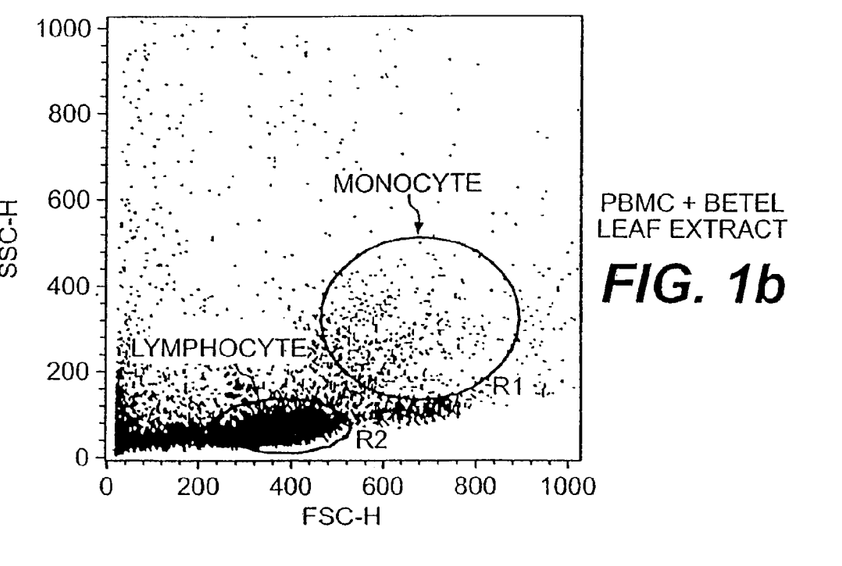
Figure 2:
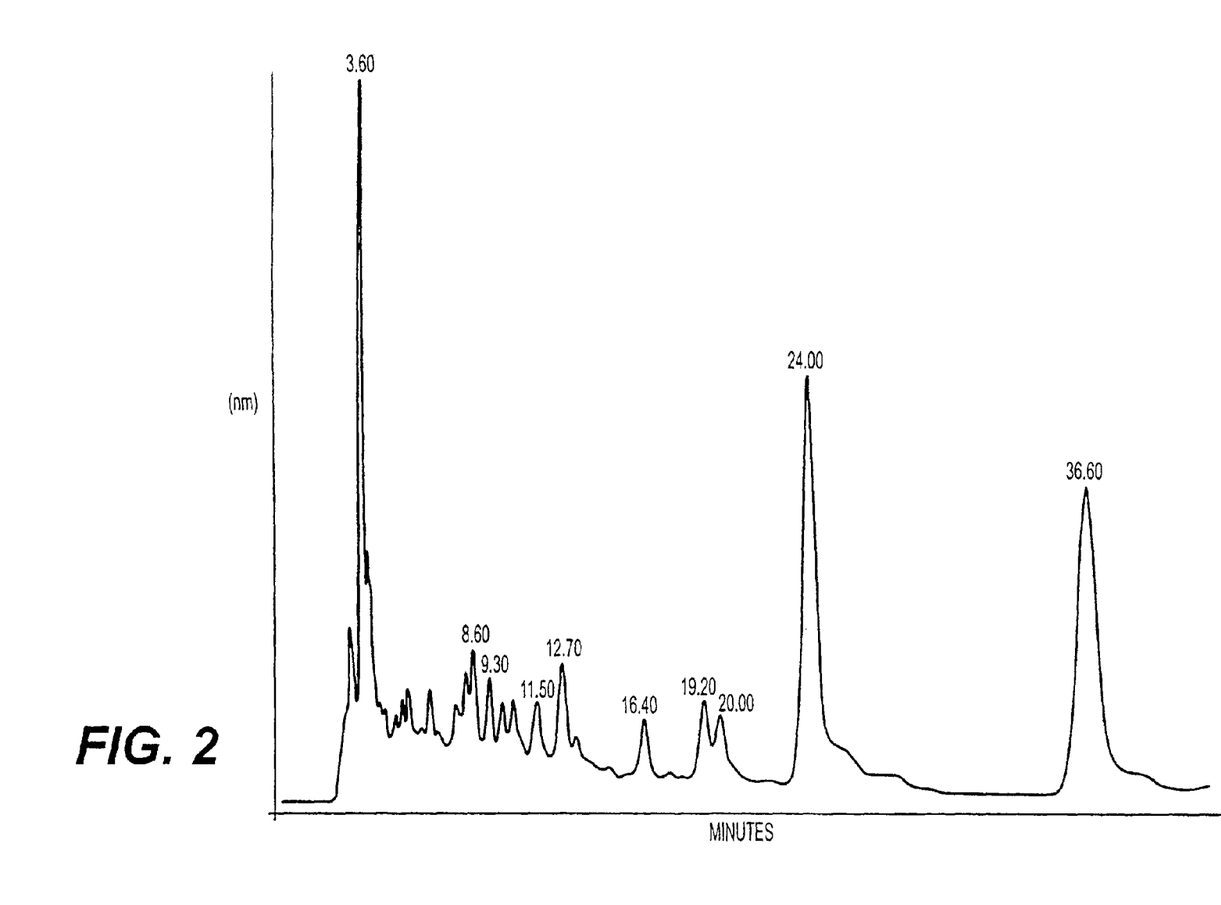
FIG. 2 represents HPLC analysis of fraction E. The first peak having retention time 3.6 min is designated as fraction 1, retention time 24.0 is designated as fraction 9; the x axis represents retention time (minutes) and the y axis represents absorbance in terms of wavelength (nm).

As shown in FIG. 1A, peripheral blood mononuclear cells had expected proportion of monocytes (R1) and lymphocytes (R2). In contrast hPBMC incubated overnight with *betel* leaf extract (wild type) had unaffected lymphocytes (FIG. 1B, R2), but had almost complete disappearance of monocytes (FIG. 1B, R1). It appears that the *betel* leaf reduces viability of monocytes by at least 80%.

(e) Discussion

Thus, our results suggest that anti-Monocytic property of *betel* leaf extract could be exploited for treatment of myeloid leukemia.

EXAMPLE 4

Collection of Plant Material

The leaves and all other plant parts of *Piper betel* were collected from the climber from different areas and West Bengal, India. A voucher specimen was deposited at the Dept. of Medicinal Chemistry at the Indian Inst. of Chemical Biology, 4 Raja S. C. Mullick Road, Kolkata-700 032.

EXAMPLE 5

Fresh leaves 5.3 kgs of *Piper betel* is thoroughly washed with distilled water. Leaves are cut into small pieces. It is then homogenized with distilled water 1.5 liter in a mixture-blender. The extract was filtered through a fine cheese-cloth and the filtrate was collected. The plant material inside the cloth was again extracted with water (1000 ml). The extract was filtered in a similar way. This process of extraction was repeated three times. The combined extract was centrifuged to obtain a clear solution. The clear extract was lyophilized yielding a semi-solid mass 150 gms. The extract was then tested for biological activity.

A potion (10.02 gm) of the extract was fractionated on Sephadex LH-20 column chromatography. The column was eluted with water, water-methanol (1:1) and methanol as eluent to give three fractions, fractions 1-3, in the order of elution. The three fractions were then tested for biological activity.

The fraction-2 (designated as Fraction E) showed biological activity, i.e., destruction of myeloid cells in human patients' ex vivo blood. Thin layer chromatography of this fraction showed two spots having Rf. 0.50 and 0.41 in the solvent system n-butanol:acetic acid:water (13:3:5). The HPLC analysis of this fraction showed several peaks as in FIG. 2 using Intersil ODS-3 (4.6×250 mm) analytical column, with a solvent system methanol:water:acetic acid (23:76:1), having flow rate of 1.0 ml/min and detection at 280 nm. With the retention time 3.60, 8.60, 9.30, 11.50, 12.70, 16.40, 19.20, 20.00, 24.00 and 36.60 mins respectively.

Each peak of this fraction E was separated in a preparative HPLC using μ-Bonda pak column (19×300 mm), with a flow rate 12 ml/min and the detection at 280 nm. Compounds isolated from individual peak were tested for biological activity as described above. A purified compound was isolated from the peak having retention time 24.00 min. The structure of the compound was established as 3-O-p-coumaryl quinic acid (FIG. 3), mp. 245 to 247° C., $[\alpha]_D$ −75° (methanol).

Figure 3:
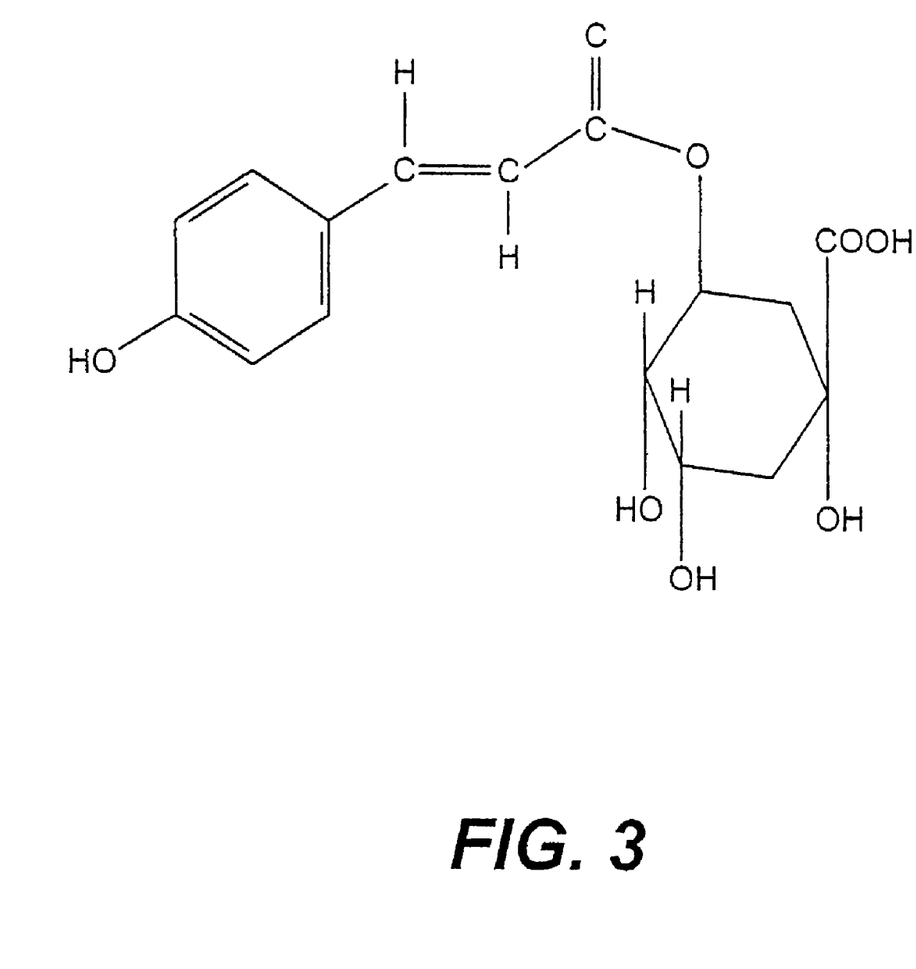
FIG. 3 represents structure of fraction 9 deduced as 3-O-p-coumaryl quinic acid.
Figure 4A:
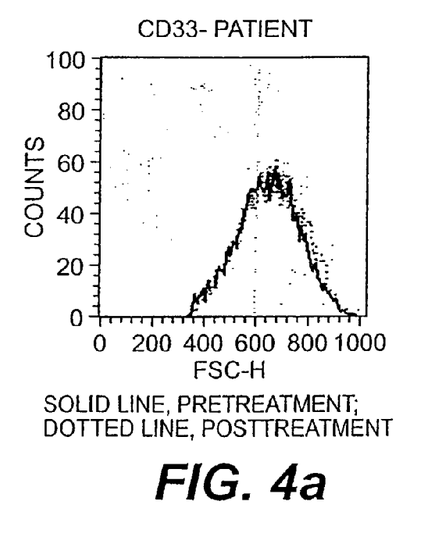
Figure 4B:
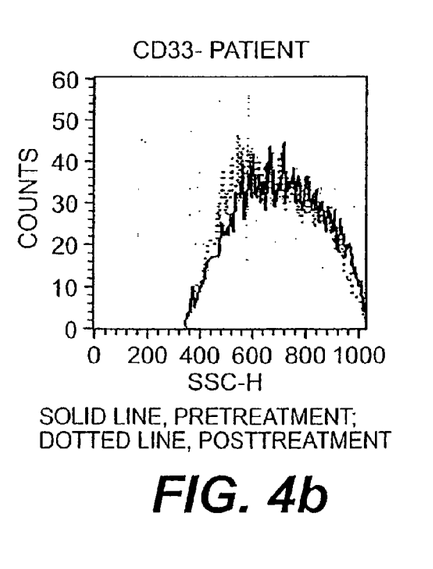
Figure 4C:
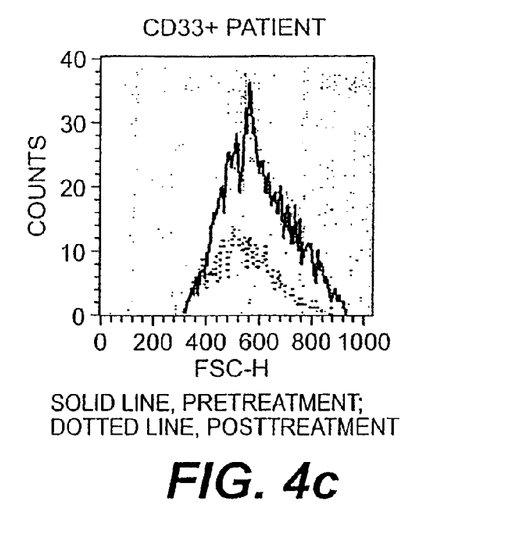
Figure 4D:
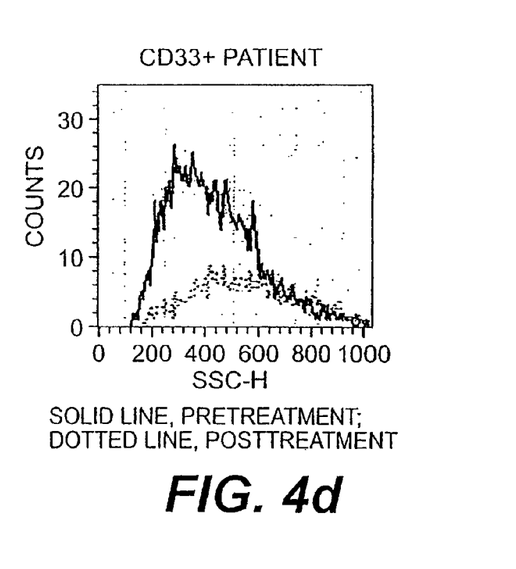
Figure 5A:
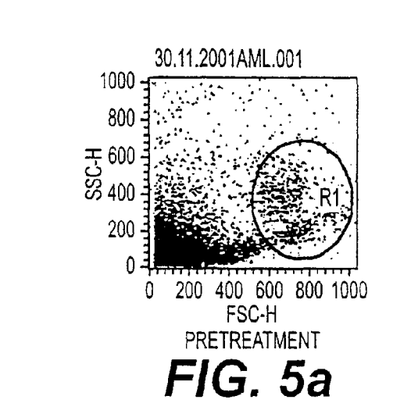
FIG. 5(a) represents dot plot of forward scatter vs. side scatter in CD 33+ AML cells before treatment with fraction E.
Figure 5B:
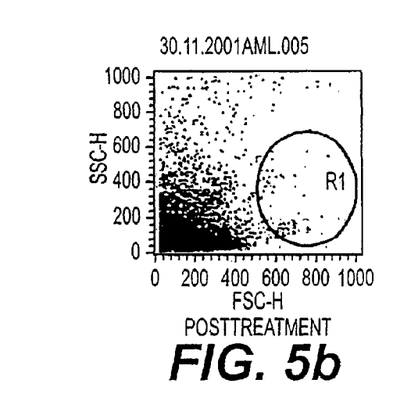
FIG. 5(b) represents dot plot of forward scatter vs. side scatter in CD 33+ AML cells after treatment with fraction E.
Figure 5C:
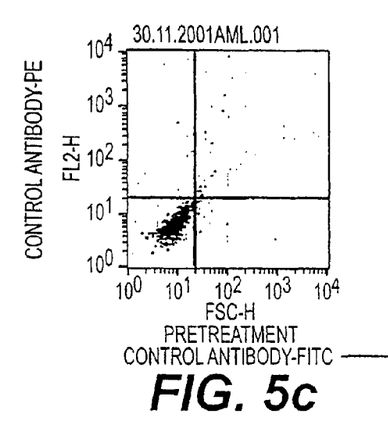
FIG. 5(c) represents dot plot of CD 33+ AML cells on staining with control antibodies, before treatment with fraction E.
Figure 5D:
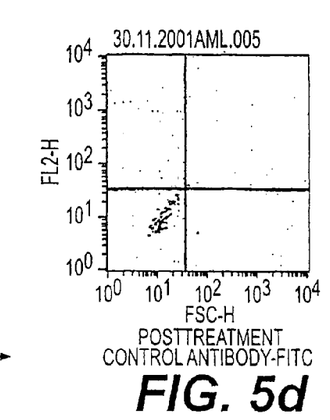
FIG. 5(d) represents dot plot of CD 33+ AML cells on staining with control antibodies after treatment with fraction E.
Figure 5E:
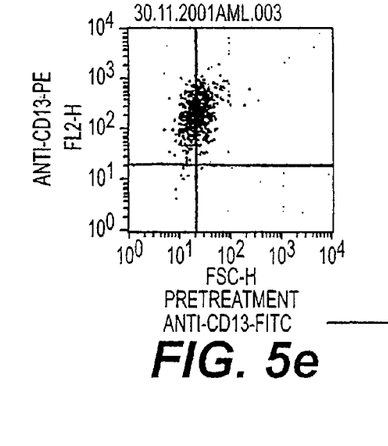
FIG. 5(e) represents dot plot of CD 33+ AML cells on staining with FITC conjugated anti-CD33 and PE-conjugated anti-CD13 monoclonal antibodies before treatment with fraction E.
Figure 5F:
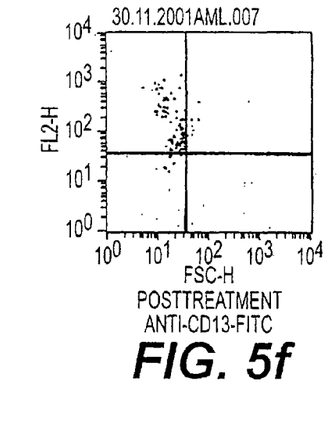
FIG. 5(f) represents dot plot of CD 33+ AML cells on staining with FITC conjugated anti-CD33 and PE-conjugated anti-CD13 monoclonal antibodies after treatment with fraction E.
Figure 6A:
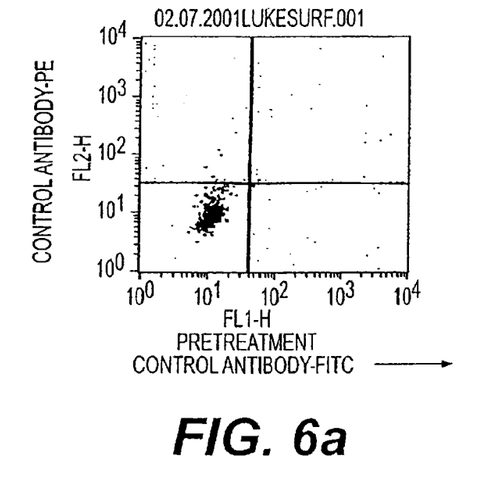
FIG. 6(a) represents dot plot of CD33− myeloid leukemic cells with control antibodies before treatment with fraction E.
Figure 6B:
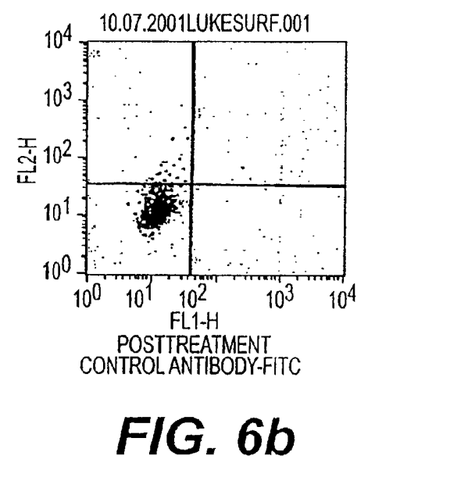
FIG. 6(b) represents dot plot of CD33− myeloid leukemic cells with control antibodies after treatment with fraction E.
Figure 6C:
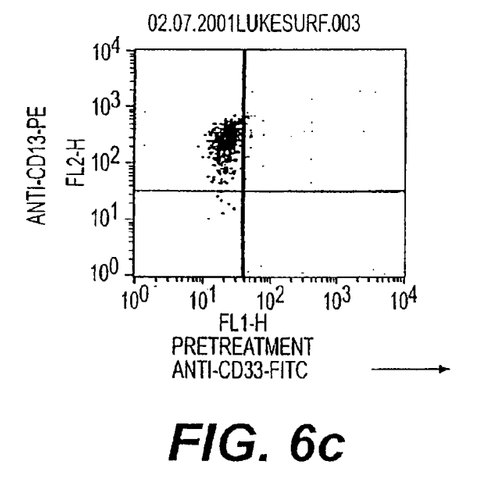
FIG. 6(c) represents dot plot of CD33− myeloid leukemic cells with anti-CD33-FITC and anti-CD13-PE monoclonal antibodies before treatment with fraction E.
Figure 6D:
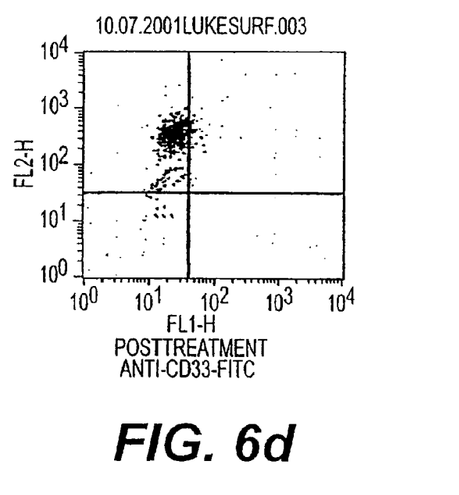
FIG. 6(d) represents dot plot of CD33− myeloid leukemic cells with anti-CD33-FITC and anti-CD13-PE monoclonal antibodies after treatment with fraction E.
Figure 7:
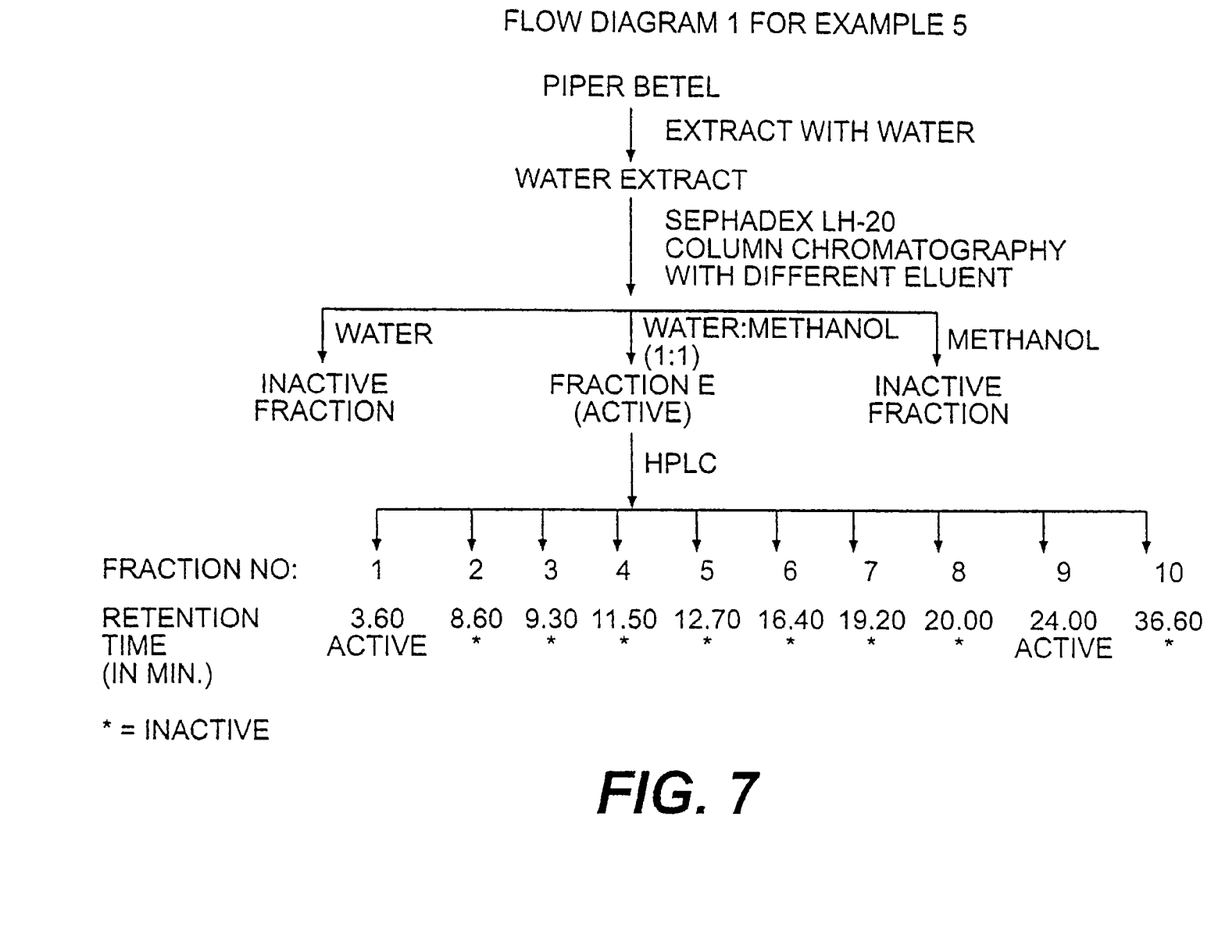
FIG. 7 represents flow diagram for example 5
Figure 8:
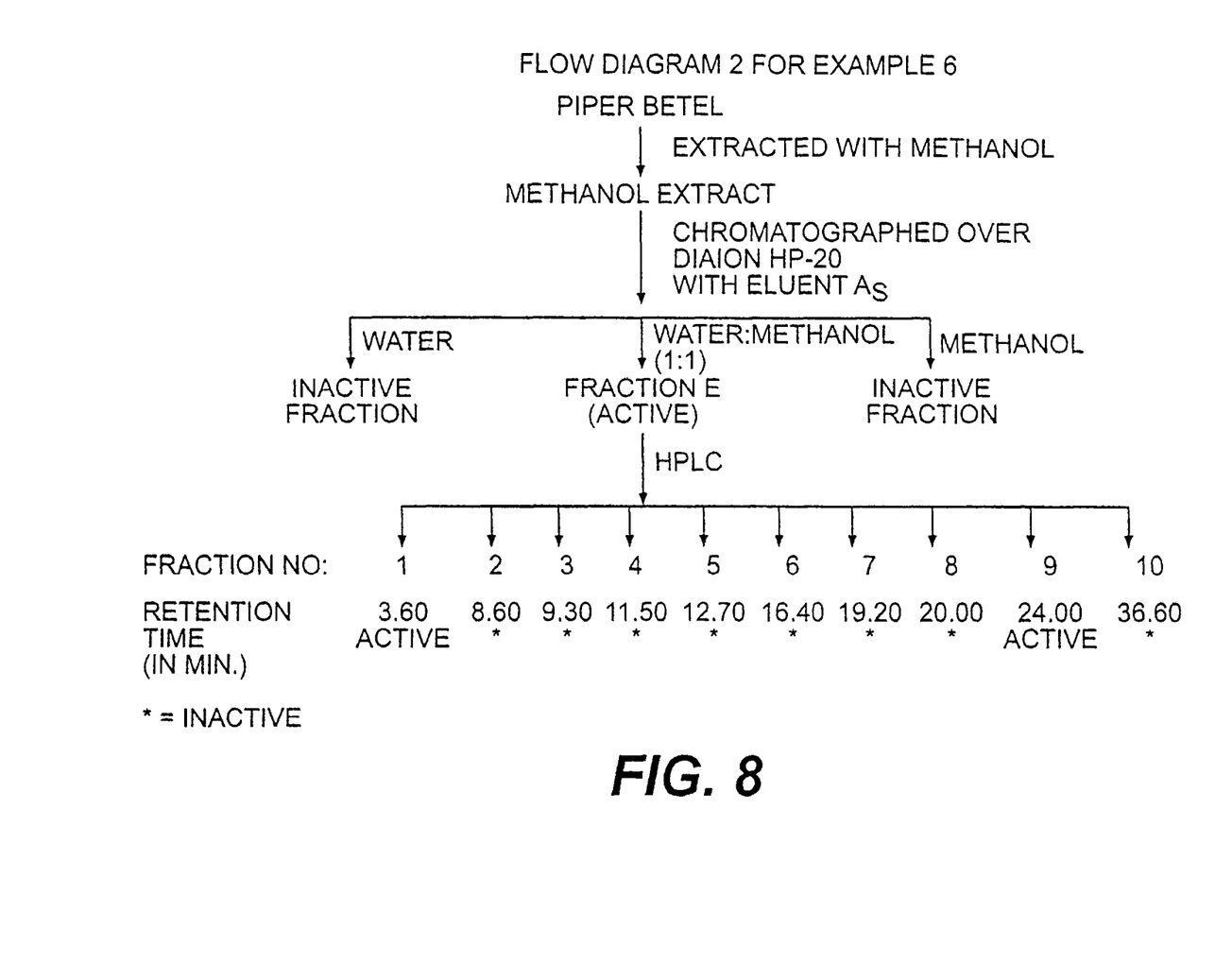
FIG. 8 represents flow diagram for example 6

| | |
|---|---|
| IR $\gamma^{KBr}_{max}$ cm$^{-1}$ | :3379 (OH), 1691 (CO), 1514, 1383, 1269, 1173 and 830 |
| $^1$H-NMR (CD$_3$OD) | 7.64 (1H, DJ = 15.9, H-7), 7.46 (2H, d, J = 8.4, H-2 and 6), 6.81 (2H, d, J = 8.4, H-3 and 5), 6.35 (1H, d, J = 15.9, H-8), 5.38 (1H, m, H-3), 4.19 (1H, br., H-4) 3.84 (1H, m, H-5), 2.2 (2H, br., H-2) and 2.0 (2H, br., H-6) |
| $^{13}$C-NMR (CD$_3$OD) | 176.00 (COOH), 167.65 (C-9), 160.24 (C-4), 145.68 (C-7), 130.17 (C-2 and 6), 126.25 (C-1), 115.81 (C-3 and 5), 75.16 (C-1'), 72.48, 70.98, 70.57, 37.79 and 37.22 |
| FAB MS m/z | 329 (M$^+$ + H), 361 (M$^+$ + Na), 377 (M$^+$ + K) |

EXAMPLE 6

The fresh leaves and all other plant parts of *Piper betel* (1.2 kg) was homogenized with methanol (800 ml) in a mixture-blender and then sonicated in an ultrasonic bath with 3 burst each for 15 min and allowed to be extracted over night for 16 hrs. Filtering through Whatman No. 1 filter paper separated the methanol-extracted material. The process of extraction was repeated for three times. The combined extract was evaporated to dryness in a flash evaporator under reduced pressure at 40° C. The residual substance was then dried under high vacuum and the semi-solid mass (35.22 gm) was tested for biological activity (as mentioned above).

The methanol extract (14 gm) was chromatographed on Diaion HP-20 (380 gm), elution being carried out with water, water-methanol (1:1) and methanol. Eluted three fractions were tested for biological activity.

HPTLC of water-methanol fraction (fraction E) showed similar Rf values (0.5 and 0.41) as described in example. Active compound, 3-O-p-coumaryl quinic acid was isolated from the fraction E by using preparative HPLC as described in example-5.

EXAMPLE 7

Preparation of Peripheral Blood Mononuclear Cells (PBMC) from CD33+ Myeloid Leukemia Patients Ex Vivo Blood Whole blood (10 ml) was drawn from a previously diagnosed CD33+ myeloid leukemic patient and mononuclear cells were separated by Ficoll/hypaqal density gradient centrifugation.

EXAMPLE 8

PBMC from CD33$^-$ Myeloid Leukemia Patients

Whole blood (10 ml) was drawn from a previously diagnosed CD33$^-$ myeloid leukemia patient. Mononuclear cells were separated by Ficoll/hypaque density gradient centrifugation.

EXAMPLE 9

Incubation of PBMC of myeloid leukemia patients with crude *Piper betel* extract. PBMC (2×10$^6$/ml) of myeloid leukemia patients were incubated with *Piper betel* extract (10.0 mg/ml) for 48 hours and then washed and counted for viability.

EXAMPLE 10

Incubation of PBMC of myeloid leukemia patients with fraction E in vitro. PBMC (2×10$^6$/ml) of myeloid leukemia patients were incubated with varied concentrations of fraction E for 48 hours. Cells were then washed and counted for viability.

EXAMPLE 11

Incubation of PBMC of myeloid leukemia patients with purified compound 3-O-p-coumaryl quinic acid in vitro. PBMC ($2\times10^6$/ml) of myeloid leukemia patients were incubated with varied concentrations of purified compound for 48 h. Cells were then washed, and counted for viability.

EXAMPLE 12

Flow cytometry of myeloid leukemia cells; Myeloid leukemia cells before and after in vitro incubation with crude *Piper betel* extract, purified fraction E or purified 3-O-p-coumaryl quinic acid were marked with anti-CD33-FITC and anti-CD13-PE monoclonal antibodies. Cells were then analysed in a flow cytometer (FACS Calibur, Bection Dickinson, USA)

EXAMPLE 13

Incubation of myeloid leukemic cells with fractions having retention time 3.60 (fraction-1) and 24.00 min (fraction 9). PBMC of myeloid leukemic patients were incubated with above-mentioned fractions, alone or in combination of the two for 48 hrs. Cells were then washed and counted for viability.

Results of the Experiments:
For Example 9
As shown in FIGS. 4(*a*), 4(*b*), 4(*c*) and 4(*d*), CD33+ myeloid leukemia cells were killed in the presence of crude *Piper betel* extract. On the other hand, crude *Piper betel* extract has no effect on the CD33⁻ myeloid leukemic cells.
For Example Nos. 10, 11, and 12
As shown in FIGS. 5(*a*), 5(*b*), 5(*c*), 5(*d*), 5(*e*) and 5(*f*), CD33+ myeloid leukemia cells are destroyed by fraction E. On the other hand, CD33⁻ myeloid leukemia cells remained unaffected. (FIG. 6).
PBMC of CD33+ myeloid leukemia patients (both AML and CML) are destroyed by purified compound 3-O-p-coumaryl quinic acid (Table-1).
For Example No. 13
As shown in Table 2 combining fractions of 1 and 9 produced greater effects as compared to their individual activity at lower concentration.

TABLE 1

Growth inhibition of AML and CML cells in vitro by purified compound

| Type of myeloid leukemia | Percent inhibition of growth by purified compound 3-O-p-coumaryl quinic acid | |
| --- | --- | --- |
| | 100 µg/ml | 600 µg/ml |
| AML | 53.37 | 100.00 |
| CML | 2.53 | 79.50 |

TABLE 2

Growth inhibition of AML cells in vitro by fractions 1 and 9

| Type of myeloid leukemia | Fractions | Percent inhibition of growth | |
| --- | --- | --- | --- |
| | | Doses (µg/ml) | % Inhibition |
| AML | 1 | 100 | 79.50 |
| | 9 | 100 | 54.00 |
| | 1 + 9 | 50 + 50 | 100.00 |

While preferred embodiments of our invention have been shown and described with specificity for purposes of 35 U.S.C. §112, the invention is to be defined solely by the scope of the appended claims.

The invention claimed is:

1. A method of treating myeloid leukemia in an animal including a human being comprising reducing levels of monocytes by administering to an animal in need thereof a pharmaceutically effective amount of a *Piper betel* leaf extract.

2. A method as claimed in claim 1, wherein the *Piper betel* leaf extract is combined with with a pharmaceutically acceptable additive.

3. A method as claimed in claim 2, wherein the additive does not interfere with activity of *Piper betel* leaf extract against monocytes.

4. A method as claimed in claim 2, wherein the additive is selected from a group of nutrients consisting of proteins, carbohydrates and sugar, talc, magnesium stearate, cellulose, calcium carbonate, starch-gelatin paste and/or pharmaceutically acceptable carriers.

5. A method as claimed in claim 1, wherein the *Piper betel* leaf extract is administered orally or intramuscularly.

6. A method as claimed in claim 5, wherein an oral administration is in the form of capsule, syrup, concentrate, powder or granules.

7. A method as claimed in claim 2, wherein the ratio of *Piper betel* leaf extract to the additive is in the range between 1-10:10-1.

8. A method as claimed in claim 1, wherein the *Piper betel* leaf extract is administered at a dosage level between 5 to 20 mg/kg of body weight for alternate days for one month.

9. A method as claimed in claim 1, wherein the pharmaceutically effective amount is an amount which reduces viability of monocytes at least by 80%.

10. A method of providing anti-monocytic activity in blood cells of an animal comprising administering to an animal in need thereof a pharmaceutically effective amount of a composition comprising *Piper betel* leaf extract to provide antmonocytic activity in the blood cells.

11. A method of destroying monocytes present in human peripheral mononuclear cells (PBMCs) comprising treating human PBMCs with a pharmaceutically effective amount of (i) a *Piper betel* leaf extract, (ii) a lyophilized *Piper betel* leaf extract or (iii) a composition comprising a *Piper betel* leaf extract for destroying monocytes.

12. A method as claimed in claim 11, wherein the composition comprising *Piper betel* leaf extract is combined with a pharmaceutically acceptable additive.

13. A method as claimed in claim 12, wherein the additive does not interfere with the destroying of monocytes by the *Piper betel* leaf extract.

14. A method as claimed in claim 12, wherein the additive is selected from a group of nutrients consisting of proteins, carbohydrates, sugar, talc, magnesium stearate, cellulose, calcium carbonate, starch-gelatin paste and/or pharmaceutically acceptable carriers.

15. A method as claimed in claim 11, wherein the *Piper betel* leaf extract or the composition is administered orally or intramuscularly.

16. A method as claimed in claim 15, wherein the oral administration is in the form of capsule, syrup, concentrate, powder or granules.

17. A method as claimed in claim 12, wherein the ratio of *Piper betel* leaf extract to the additive is in the range between 1-10:10-1.

18. A method as claimed in claim 11, wherein the *Piper betel* leaf extract is obtained by crushing *Piper betel* leaves to obtain a crushed leaves and extracting the crushed leaves with water or organic solvents selected from the group consisting of alcohol, carbon tetrachloride, chloroform and acetone.

19. A method as claimed in claim 11, wherein the *Piper betel* leaf extract or the composition is administered at a dosage level between 5 to 20 mg/kg of body weight for alternate days for one month.

20. A method as claimed in claim 11, wherein the pharmaceutically effective amount is an amount which reduces viability of monocytes at least by 80%.

* * * * *